(12) United States Patent
Bottlang

(10) Patent No.: US 8,197,523 B2
(45) Date of Patent: Jun. 12, 2012

(54) BONE SCREW FOR POSITIVE LOCKING BUT FLEXIBLE ENGAGEMENT TO A BONE

(75) Inventor: Michael Bottlang, Portland, OR (US)

(73) Assignee: Apex Biomedical Company, LLC, Lake Oswego, OR (US)

( * ) Notice: Subject to any disclaimer, the term of this patent is extended or adjusted under 35 U.S.C. 154(b) by 1275 days.

(21) Appl. No.: 11/058,935

(22) Filed: Feb. 15, 2005

(65) Prior Publication Data

US 2006/0195099 A1    Aug. 31, 2006

(51) Int. Cl.
*A61B 17/04*    (2006.01)

(52) U.S. Cl. ......... 606/312; 606/301; 606/305; 606/311

(58) Field of Classification Search ............. 606/62, 606/63, 65–68, 286–289, 291, 300–320; 411/374, 389, 395, 397, 399, 410, 412, 413, 411/416, 418, 426

See application file for complete search history.

(56) References Cited

U.S. PATENT DOCUMENTS

| | | | | |
|---|---|---|---|---|
| 4,959,064 A * | 9/1990 | Engelhardt | | 606/65 |
| 4,978,350 A * | 12/1990 | Wagenknecht | | 606/312 |
| 5,015,134 A * | 5/1991 | Gotoh | | 411/386 |
| 5,053,036 A | 10/1991 | Perren et al. | | |
| 5,382,195 A | 1/1995 | Hiler | | |
| 5,709,686 A | 1/1998 | Talos et al. | | |
| 5,725,581 A | 3/1998 | Brånemark | | |
| 5,741,258 A | 4/1998 | Kkaue et al. | | |
| 5,954,722 A | 9/1999 | Bono | | |
| 6,129,730 A * | 10/2000 | Bono et al. | | 606/291 |
| 6,238,417 B1 * | 5/2001 | Cole | | 606/213 |
| 6,270,499 B1 * | 8/2001 | Leu et al. | | 606/64 |
| 6,306,140 B1 * | 10/2001 | Siddiqui | | 606/315 |
| 6,309,393 B1 | 10/2001 | Tepic et al. | | |
| 6,558,387 B2 | 5/2003 | Errico | | |
| 6,595,993 B2 | 7/2003 | Donno et al. | | |
| 6,712,820 B2 * | 3/2004 | Orbay | | 606/286 |
| 7,294,130 B2 * | 11/2007 | Orbay | | 606/291 |
| 7,637,928 B2 * | 12/2009 | Fernandez | | 606/289 |
| 7,695,472 B2 * | 4/2010 | Young | | 606/70 |
| 2002/0142265 A1 | 10/2002 | Weissman | | |
| 2002/0156474 A1 * | 10/2002 | Wack et al. | | 606/69 |
| 2002/0198527 A1 * | 12/2002 | Muckter | | 606/73 |
| 2004/0071527 A1 | 4/2004 | Dendo | | |
| 2004/0172030 A1 * | 9/2004 | Tipirrneni | | 606/72 |
| 2004/0230195 A1 | 11/2004 | Kaikkonen | | |
| 2004/0260291 A1 | 12/2004 | Jensen | | |
| 2005/0010224 A1 * | 1/2005 | Watkins et al. | | 606/65 |
| 2005/0010226 A1 * | 1/2005 | Grady et al. | | 606/69 |
| 2005/0085818 A1 * | 4/2005 | Huebner | | 606/69 |
| 2005/0101961 A1 * | 5/2005 | Huebner et al. | | 606/72 |
| 2005/0154390 A1 | 7/2005 | Biedermann | | |
| 2005/0216005 A1 | 9/2005 | Howland | | |

(Continued)

FOREIGN PATENT DOCUMENTS

EP    0 355 035 B1    5/1994

(Continued)

*Primary Examiner* — Eduardo C Robert
*Assistant Examiner* — Tara Carter
(74) *Attorney, Agent, or Firm* — Schwabe, Williamson & Wyatt

(57) ABSTRACT

A bone screw having a head portion and an adjoining shaft portion is described. The shaft portion has a front, a mid, and a neck section, where at least two of the sections having complementary features and/or attributes to facilitate positive-locking, but flexible engagement of the bone screw to a bone.

34 Claims, 3 Drawing Sheets

U.S. PATENT DOCUMENTS

| | | |
|---|---|---|
| 2005/0240190 A1 * | 10/2005 | Gall et al. .................. 606/72 |
| 2005/0266383 A1 | 12/2005 | Aravena et al. |
| 2005/0277940 A1 * | 12/2005 | Neff ........................... 606/73 |
| 2006/0004361 A1 | 1/2006 | Hayeck et al. |
| 2006/0116678 A1 | 6/2006 | Impellizzeri |
| 2006/0129147 A1 | 6/2006 | Biedermann et al. |
| 2006/0173462 A1 | 8/2006 | Kay et al. |
| 2006/0195099 A1 | 8/2006 | Bottlang |
| 2007/0016200 A1 | 1/2007 | Jackson |
| 2007/0233071 A1 | 10/2007 | Dewey et al. |
| 2008/0140076 A1 | 6/2008 | Jackson |
| 2009/0062868 A1 | 3/2009 | Casutt |
| 2009/0171403 A1 * | 7/2009 | Tipirneni ................. 606/86 R |

FOREIGN PATENT DOCUMENTS

| | | |
|---|---|---|
| FR | 742.618 | 1/1933 |
| WO | WO 89/04150 | 5/1989 |
| WO | 2004112587 A | 12/2004 |

* cited by examiner

BONE SCREW FOR POSITIVE LOCKING BUT FLEXIBLE ENGAGEMENT TO A BONE

TECHNICAL FIELD

The present invention relates generally to the field of medical devices. In particular, embodiments of the present invention relate, but are not limited, to a bone screw with features and/or attributes to provide positive-locking but flexible engagement to a bone.

BACKGROUND

Bone screws have typically been used to directly compress osteosynthesis plates onto the bone in order to align and stabilize a bone fracture. In this utilization, bone screws are not fixed rigidly to the bone plate, and the resulting frictional force between the plate and the bone is solely responsible for the stability of the osteosynthesis construct. Loosening of the screws in the bone or a resorption of the bone can thus easily lead to a loss of stability.

To avoid such loosening, and for the purpose of improving vascularity in a manner that minimizes damage to the bone surface, means for rigid locking of a bone screws in a bone plate and elevated fixation of a bone plate over the bone surface have been introduced. For example, in one prior art implementation, a positive-locking system between the screw and plate is effectuated by means of a bone plate with conical plate holes. The conical plate holes provide a rigid connection between the plate and the fixation screws, even after the screw-bone interface has loosened. In another prior art implementation, a positive-locking system is effectuated by fitting screw holes in the plate with inside threads. These threaded holes accept bone screws fitted with a second threaded portion which is widened compared to the conventional threaded screw shank segment, to facilitate engagement with the inside thread of the plate hole. These prior art positive-locking screws are designed to be threaded into the first bone surface underlying the plate, or into both the first and second bone surface of a quasi-cylindrical bone cross-section underlying the plate.

While these positive-locking osteosynthesis constructs provide superior stability, their stiffness can pose increased stress to the screw-bone interface. This has introduced failure modes, in which the bone resorbs or fractures adjacent to the outermost screw in the plate, since this screw absorbs the majority of the stress as the load is transferred from the bone to the plate.

Furthermore, the stiffness of the fixation construct suppresses small motion at the fracture site, which otherwise can be beneficial for fracture healing by inducing a fracture callus. Less stiff external fixators similarly impose positive-locking between bone pins and an external fixation bar. However, flexion of the considerably long fixation pins allows for controlled motion at the fracture site that is of sufficient magnitude to induce fracture healing by callus formation. While positive-locking plate-screw constructs employ a similar fixation principle as an external fixator, the close proximity of the plate to the bone surface prohibits elastic flexion of the screw segment between the plate and the bone.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Illustrative embodiments of the present invention include, but are not limited to, a bone screw, an osteosynthesis construct, and associated methods for using the bone screw and/or the osteosynthesis construct.

Various aspects of the illustrative embodiments will be described using terms commonly employed by those skilled in the art to convey the substance of their work to others skilled in the art. However, it will be apparent to those skilled in the art that alternate embodiments may be practiced with only some of the described aspects. For purposes of explanation, specific numbers, materials, and configurations are set forth in order to provide a thorough understanding of the illustrative embodiments. However, it will be apparent to one skilled in the art that alternate embodiments may be practiced without the specific details. In other instances, well-known features are omitted or simplified in order not to obscure the illustrative embodiments.

The phrase "in one embodiment" is used repeatedly. The phrase generally does not refer to the same embodiment; however, it may. The terms "comprising", "having" and "including" are synonymous, unless the context dictates otherwise.

Figure 1:
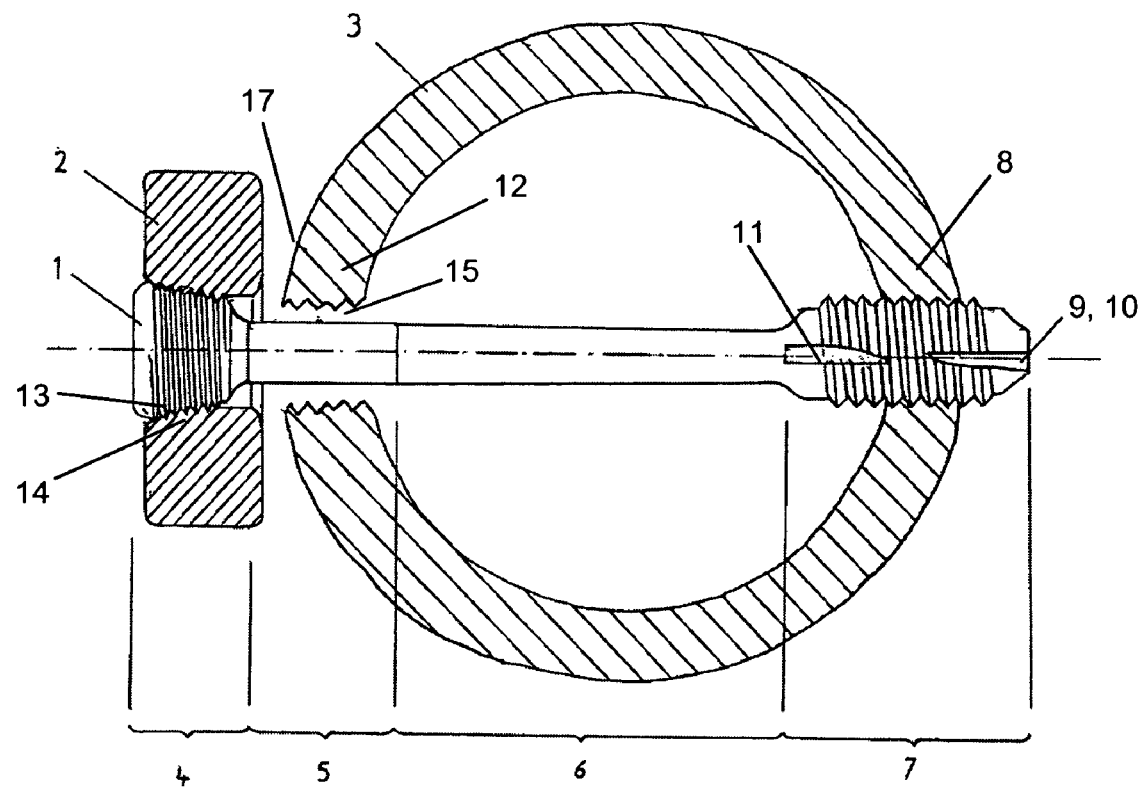
FIG. 1 shows a side-view of a bone screw, in accordance with one aspect and some embodiments of the invention, in association with a transverse cross-section of a tubular bone segment and a bone plate.

Referring now to FIG. 1, illustrated therein is bone screw 1 in accordance with various embodiments and one aspect of the present invention. Additionally, bone screw 1 is illustrated with a cross section view of tubular bone 3 and bone plate 2. As illustrated, for the embodiments, bone screw 1 includes a head portion 4 and an adjoining shaft portion having a front section 7, a mid section 6, and a neck section 5. As will be described in more detail below, in various embodiments, at least two of sections 5-7 are endowed with complementary features and/or attributes, such that bone screw 1 may be positively-locked, but flexibly engaged to a bone. Additionally, bone screw 1 may be employed in conjunction with bone plate 2 to form an osteosynthesis construct. Further, potential advantages that may be obtained from adapting, and using bone screw 1 will also be described below.

For the embodiments, bone screw 1 is a rotationally symmetrical unitary piece having a central axis, depicted by the dotted line running from head portion 4 through the neck, mid and front sections 5-7 of the shaft portion. In various embodiments, bone screw 1 is made of a biocompatible material, e.g. stainless steel or titanium.

For the illustrated embodiments, front section 7 has a core diameter of d1, and is threaded for secure fixation of bone screw 1 in the far bone surface, termed far cortex 8. The length of threaded front section 7 is sufficient to span or exceed the thickness of far cortex 8.

Further, for the illustrated embodiments, threaded front section 7 may incorporate a self-tapping feature 9, which allows for insertion of bone screw 1 without the need for tapping of a screw thread. Additionally, for the illustrated embodiments, threaded front section 7 may also incorporate a self-drilling feature 10, which allows for screw insertion without the need for pre-drilling a hole in the cortex. Still further, for the illustrated embodiments, threaded front section 7 may also incorporate a second self-drilling feature 11 located toward mid section 6, which allows for screw removal (withdrawal) to penetrate newly formed bone at the perimeter of the screw hole (cavity) 15 in the near cortex 12.

Still referring to FIG. 1, mid section 6 of the shaft portion has a diameter d2. The diameter d2 may be constant, or may alter towards the neck section 5 in a manner to induce essentially evenly distributed bending and strain along mid section 6 as a load perpendicular to the central axis of bone screw 1 is applied to head portion 4 of bone screw 1. The diameter d2 may be as large as the core diameter of the threaded front section, or may be as small as 50% of the core diameter of the threaded front section 7. The length of mid section 6 extends through a substantial portion of the distance between the near and far cortex.

The geometry of mid section 6 effectively determines the stiffness for the connection between bone 3 and bone plate 2. In various embodiments, the geometry is selected such that mid section 6 has a bending ability to accommodate flexion along the central axis of bone screw 1, to allow for controlled relative motion between bone 3 and bone plate 2. In various embodiments, the bending ability is sufficient to accommodate excessive loading of the osteosynthesis construct. In such event, mid section 6 provides for a controlled failure mechanism to delay or prevent more detrimental failure modes, such as plate bending or bone fracture. Further, this elasticity may also improve the ability of head portion 4 to engage bone plate 2, especially for embodiments where engagement involves engaging threads 13 of head portion 4 with threaded through hole 14 of bone plate hole 2, and the "screw holes" in the bone and threaded through hole 14 of bone plate 2 are not precisely concentric.

The exact geometric attributes of mid section 6 is application dependent, that is, it may vary from one application to another. Further, for the illustrated embodiments, mid section 6 is illustrated as being unthreaded. In alternate embodiments, mid section 6 may be threaded instead.

Continuing to refer to FIG. 1, neck section 5 has a core diameter of d4 and spans the width of near cortex 12 without being rigidly fixed in near cortex 12, with near cortex 14 being the bone surface underlying bone plate 2. The diameter d4 may be as large as the core diameter of threaded front section 7, and may be as small as 50% of the core diameter of threaded front section 7. The diameter d4 is smaller than the diameter d5 of screw hole 15 in the near cortex. The difference between d4 and d5 determines the amount of flexion the screw shaft will accommodate before neck section 5 contacts screw hole 15 in near cortex 12.

The resulting axial and translational degree of freedom between screw neck 5 and screw hole 15 in the near cortex plays a significant role in realizing the benefits of far cortex fixation, including reduction of construct stiffness and reduction of stress concentrations at the screw-bone interface. Contact of the screw shaft with near cortex 12 due to increased loading of the osteosynthesis construct may provide additional support, and may dynamically increase construct stiffness.

Figure 2:
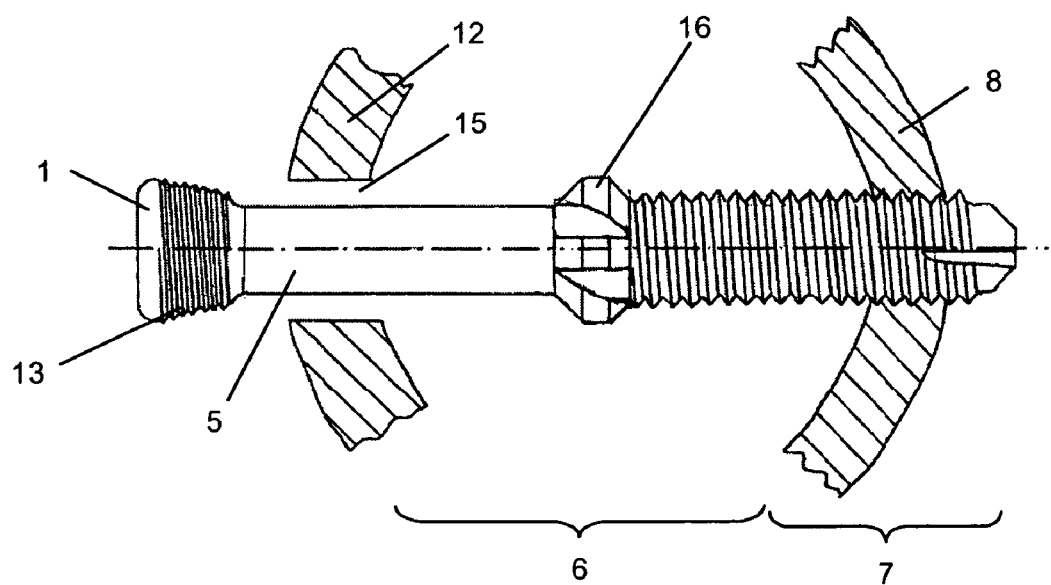
FIG. 2 shows a side-view of the bone screw, in accordance with other embodiments.

Referring now also to FIG. 2, wherein various alternate embodiments of bone screw 1 are illustrated. For these alternate embodiments, instead of the reduced neck diameter design shown in FIG. 1, alternative means to achieve the desired degree of freedom between the neck section 5 and near cortex 12 are employed. For the embodiments, mid section 6 is provided with a short, elevated cutting flute 16 of diameter d3. The diameter is at least as big as the outer diameter of threaded front section 7, and may be up to twice as big as the outer diameter of threaded front section 7. Thus, during screw insertion, cutting flute 16 will further expand the diameter of screw hole 15 in near cortex 12, initially established with a smaller diameter for allowing front section 7 to pass through, to ensure that neck section 5 of bone screw 1 is not rigidly fixed in near cortex 12. During screw removal/withdrawal, cutting flute 16 will again expand screw hole 15 in near cortex 12 to remove newly formed bone.

Referring now to both FIGS. 1 and 2, for the illustrated embodiments, head portion 4 is provided with a conical shape, and is fitted with a threaded portion 13. In various embodiments, thread portion 13 is widened, compared to the threads of front section 7. This threaded head is adapted to engage with the inside thread 14 of plate hole 2 to form a positive-locking mechanism between bone screw 1 and bone plate 2.

While the foregoing descriptions have been presented with bone screw 1 and 2 illustrated in the context of a cross-section of a tubular bone. Those skilled in the art will appreciate that the present invention is not so limited, and may be practiced in non-tubular situation.

Still referring to FIGS. 1-2, in various applications, bone screw 1 is inserted through bone plate 2 into bone 3. More specifically, in various applications, bone screw 1 is inserted substantially perpendicular to the surface plane of bone plate 2, and is substantially aligned with the central axis of the plate hole of bone plate 2. During screw insertion, bone plate 2 may or may not be elevated from the bone surface 17. Screw insertion will terminate as soon as the threaded screw head section 4 is fully seated in the corresponding threaded plate hole 14. After screw insertion, bone plate 2 is positively locked to bone screw 1, and will maintain the elevation from the bone surface given during screw insertion.

In various applications/embodiments, two or more far cortex bone screws 1 of FIGS. 1-2 may be associated with bone plate 2 to form an osteosynthesis construct. The stiffness of the construct may be adjusted by the complementary geometry provided to the bone screws 1, and by the number of bone screws 1.

Figure 3A:
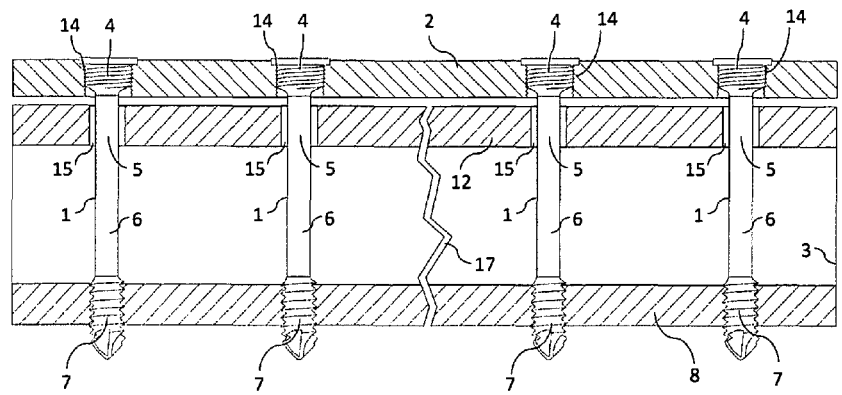
FIGS. 3a and 3b show a bone plate and bone screw construct affixed to a bone in accordance with an embodiment.
Figure 3B:
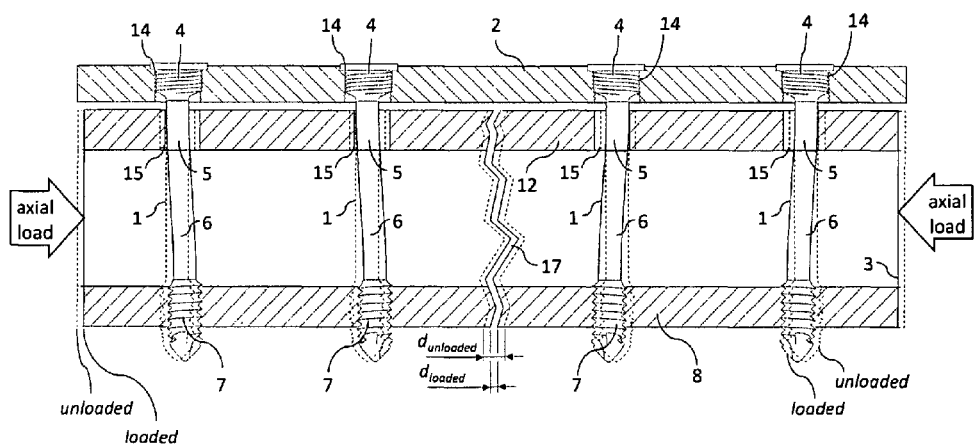

FIGS. 3*a* and 3*b* show a bone plate 2 and bone screws 1 affixed to a bone 3 for fixation of fracture 17. Each bone screw 1 includes a head portion 4 and an adjoining shaft portion having a front section 7, a mid section 6, and a neck section 5. Threaded front section 7 is configured to lock in far cortex 8. Head portion 4 is configured to engage with through holes 14 on plate 2. In a secured position, neck section 5 resides in holes 15 in near cortex 12. The configuration of FIG. 3*a* permits controlled relative motion between bone plate 2 and bone 3 and consequent motion at fracture site 17. Motion is illustrated under load in FIG. 3*b*. Screws 1 elastically deflect under load until neck sections 5 contact a side of holes 15 in near cortex 12.

In other applications/embodiments, one or more far cortex bone screws 1 of FIGS. 1-2 may be combined with one or more conventional positive-locking bi-cortical or near cortex bone screws to provide for a more gradual load transfer between the bone and the bone plate.

In still other applications/embodiments, one or more far cortex bone screws 1 of FIGS. 1-2 may be combined with one or more conventional, non-locking bi-cortical screws to improve fixation strength and durability.

Figure 4:
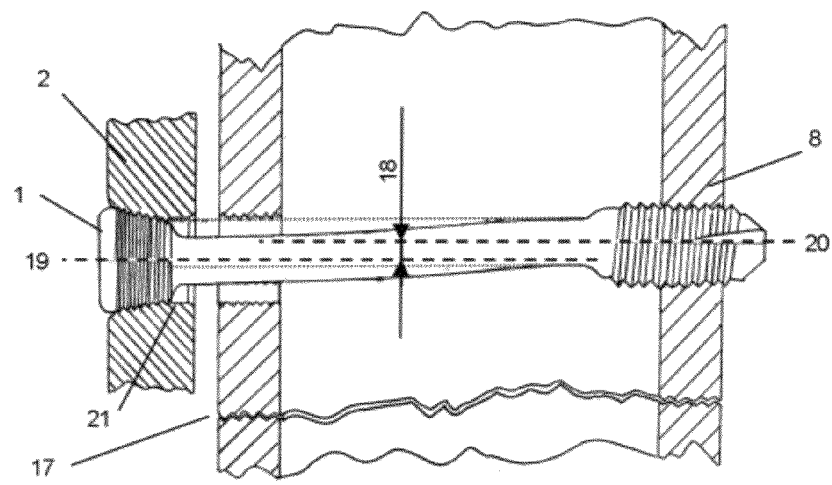
FIG. 4 shows a method for attaching a bone screw to a bone, using an embodiment of the bone screw of FIGS. 1-2, in accordance with another aspect and other embodiments of the present invention.

FIG. 4 demonstrates another implementation/application of far cortex locked screw 1 for compression of a bone fracture 17. For the implementation/application, far cortex locked screw 1 is employed to provide an offset 18 between the plate hole axis 19 and the axis 20 of the screw hole in the far cortex. To achieve compression at the fracture site 17 that is spanned by the osteosynthesis construct, bone screw 1 can be inserted in the far cortex 8 parallel to the axis of the corresponding plate hole and fracture site 17, but slightly further away from the fracture site 17 as compared to the axis of corresponding plate hole. This non-concentric screw insertion is made possible by the elastic bending ability of the screw shaft to engage the screw head into the threaded plate hole. This in turn transmits prolonged compression to fracture site 17 due to the elastic force stored in the screw shaft.

The offset between the screw hole axis 20 in far cortex 8 and the corresponding plate hole axis 19 may be in the range of 1 mm to 5 mm. Screw insertion in the far cortex under such offset may be accommodate since the screw neck is smaller in diameter than the near cortex screw hole and the plate hole 21.

Figure 5:
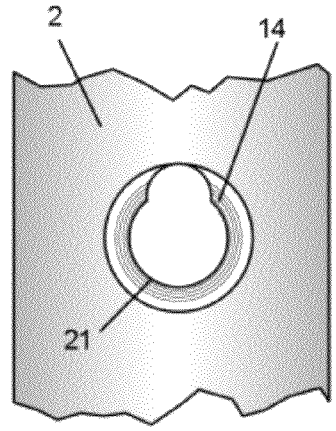
FIG. 5 shows a top view of a plate hole in accordance with other embodiments, and another aspect of the present invention, suitable for use to practice the method of FIG. 4.

In various embodiments, if a larger offset is desirable, the plate hole 21 may be adapted by elongating the hole in direction of the longitudinal plate axis, and towards the end of the plate, as depicted in FIG. 5. In other words, a portion of the circumference of the substantially circular plate hole 21 may be extended in the desired direction.

Thus, it can be seen from the foregoing description, bone screw 1, osteosynthesis construct formed used bone screw 1, and methods for using them, may provide one or more of the following advantages:

Far cortex fixation provides a less stiff, more flexible osteosynthesis construct as compared to alternative plate and screw osteosynthesis constructs.

Less stiff far cortex fixation can reduce stress concentrations in bone, which in turn can reduce the incident of bone fractures caused by the osteosynthesis construct, especially in case of osteoporotic bone.

The stiffness of the fixation construct can be adjusted by varying the number of far cortex fixation screws that connect the plate to a bone segment by means of a positive-locking mechanism.

Provision of a controlled failure mechanism by screw shaft bending to delay or prevent more detrimental failure modes, such as plate bending or bone fracture.

The flexible screw shaft improves the ability to engage the threaded screw head with the plate hole thread, especially when the screw holes in the bone and plate are not precisely concentric.

Provision of a means for fracture site compression by means of non-concentric insertion of the screw in the far cortex, so that the screw head can only engage in the plate hole thread if a force perpendicular to the screw central axis is applied to the screw head.

Although specific embodiments have been illustrated and described herein, it will be appreciated by those of ordinary skill in the art that a wide variety of alternate and/or equivalent implementations may be substituted for the specific embodiments shown and described, without departing from the scope of the present invention. This application is intended to cover any adaptations or variations of the embodiments discussed herein. Therefore, it is manifestly intended that this invention be limited only by the claims and the equivalents thereof.

What is claimed is:

1. A bone screw, comprising:
 a shaft portion having
  a front section having a core diameter and including a plurality of threads threaded around the core diameter, the threads defining an outer thread diameter, for engagement of the bone screw with the far cortex of the bone,
  a mid section, and
  a neck section having a diameter less than the core diameter of the front section, the neck section defining a portion of the shaft having a length to span a thickness of a near cortex of the bone; and
 a head portion adjoining the shaft portion and providing for engagement of the bone screw with a bone plate;
 wherein the shaft portion is integral with the head portion.

2. The bone screw of claim 1, wherein the plurality of threads span a distance equal to or greater than a thickness of the far cortex of the bone.

3. The bone screw of claim 1, further comprising at least a selected one of a tapping feature and a cutting feature provided to the front section to facilitate insertion of the shaft portion into the bone.

4. The bone screw of claim 1, further comprising a cutting feature provided to the front section to remove bone in the near cortex during withdrawal of the shaft portion from the bone.

5. The bone screw of claim 1, wherein the configuration of the shaft portion provides an amount of elastic deflection to the mid section.

6. The bone screw of claim 5, wherein the elastic deflection of the mid section provides an amount of alignment tolerance between the head portion and the bone plate.

7. The bone screw of claim 5, wherein the mid section has a diameter that is less than the core diameter of the front section.

8. The bone screw of claim 1, wherein the mid section comprises a length that spans a substantial portion of the distance between a far and a near cortex of the bone.

9. The bone screw of claim 1, further comprising a cutting feature provided to the mid section to enable concurrent establishment at a near cortex of the bone, a cavity with a diameter greater than the diameter of the neck section and greater than a diameter of the plurality of the threads on the front section, as the bone screw is inserted into the bone.

10. The bone screw of claim 9, further comprising a second cutting feature for re-establishing the cavity in the near cortex, if necessary, for withdrawal of the bone screw.

11. The bone screw of claim 1, wherein the head portion further comprises a plurality of threads adapted to engage a threaded hole of the bone plate.

12. The bone screw of claim 1, wherein the shaft and adjoining head portion of the bone screw are adapted to allow the bone screw to be attached to the bone, through the bone plate, in a manner that is substantially perpendicular to a planar surface of the bone plate.

13. The bone screw of claim 1, wherein the shaft portion and the adjoining head portion form a substantially symmetrical unitary piece.

14. An osteosynthesis construct, comprising:
 a bone plate, said bone plate having a first through hole; and
 a first bone screw, substantially as set forth in claim 1, for engaging a bone through the first through hole, to affix the first bone screw to the far cortex of the bone.

15. The osteosynthesis construct of claim 14, wherein the bone plate further has a second through hole, and the osteosynthesis construct further comprises a second bone screw, substantially as set forth in claim 1, for engaging the bone through the second through hole, the first and second bone screws having first and second complementary geometric attributes to provide or contribute to providing for a bone holding strength for the osteosynthesis construct.

16. The osteosynthesis construct of claim 14, wherein the bone plate further has a second through hole, and the osteosynthesis construct further comprises a second screw of conventional positive-locking bi-cortical or near cortical bone screw design, for engaging the bone through the second through hole.

17. The osteosynthesis construct of claim 14, wherein the bone plate further has a second through hole, and the osteosynthesis construct further comprises a second screw of conventional non-locking bi-cortical bone screw design, for engaging the bone through the second through hole.

18. The osteosynthesis construct of claim 14, wherein the first through hole has a substantially circular shape, except for a portion of its circumference extending away from a center of the first through hole.

19. A method for engaging a bone screw and a bone plate with a bone, comprising:
establishing a cavity having a diameter at a near cortex of the bone;
inserting a front section of a shaft portion of a bone screw through a through hole of a bone plate and through the cavity, and engaging the front section of the shaft portion with a far cortex of the bone such that a neck section of the shaft portion spans the cavity, wherein the front section has a core diameter and an outer thread diameter, and the neck section has a diameter less than the core diameter of the front section and less than the diameter of the cavity, the neck section defining a portion of the shaft having a length to span a thickness of a near cortex of the bone; and engaging a head portion of the bone screw with the through hole of the bone plate, wherein the shaft portion is integral with the head portion.

20. The method of claim 19, wherein said establishing comprises initially establishing the cavity with a first diameter the same size as or smaller than the core diameter of the front section, and then enlarging the cavity to a second diameter with a cutting feature present on the bone screw.

21. The method of claim 19, wherein said establishing is integrally performed when performing said inserting.

22. A method for bone fracture fixation, comprising:
engaging a front section of a shaft portion of a bone screw at a location of the bone along a first axis; and
engaging a positive locking head portion of the bone screw with a through hole of a bone plate along a second axis, wherein the first axis and the second axis are not aligned; wherein the shaft portion is integral with the positive locking head portion of the bone screw.

23. A method for fixing a bone fracture, comprising:
engaging a bone plate with a bone having a near cortex and a far cortex, said bone plate having a plurality of through holes; and
inserting a plurality of bone screws into said plurality of through holes, through the near cortex and into the far cortex, said plurality of bone screws each comprising: a shaft portion comprising: a front section, wherein the front section has a core diameter and an outer thread diameter, being locked in the far cortex of the bone, a neck section spanning a cavity formed in the near cortex while not locking in the near cortex of the bone to allow for controlled relative motion between the bone plate and the bone, wherein the neck section has a diameter less than a diameter of the cavity and less than the core diameter of the front section, the neck section defining a portion of the shaft portion having a length to span a thickness of a near cortex of the bone; and a head portion for engaging a through hole of the bone plate, wherein the shaft portion is integral with the head portion.

24. The method of claim 23, wherein said bone plate remains elevated from the bone after the plurality of bone screws are inserted into the bone.

25. The method of claim 23, wherein a difference between the diameter of the neck section and the diameter of the cavity defines an amount of flexion the plurality of screws accommodate before the plurality of screws contact sides of the cavities in the near cortex.

26. A bone screw, comprising:
a shaft portion having
a front section having a core diameter and including a plurality of threads threaded around the core diameter, the threads defining an outer thread diameter, for engagement of the bone screw with the far cortex of the bone,
a mid section having a core diameter and an outer non-threaded diameter, and
a neck section having a diameter less than the outer non-threaded diameter of the mid section, the neck section defining a portion of the shaft having a length to span a thickness of a near cortex of the bone; and
a head portion adjoining the shaft portion and providing for engagement of the bone screw with a bone plate; wherein the shaft portion is integral with the head portion.

27. The bone screw of claim 26, wherein the mid section comprises a cutting feature defining the outer non-threaded diameter to enable concurrent establishment at a near cortex of the bone, a cavity with a diameter greater than the diameter of the neck section and greater than the outer thread diameter of the front section, as the bone screw is inserted into the bone.

28. A method for engaging a bone screw and a bone plate with a bone, comprising:
establishing a cavity having a diameter at a near cortex of the bone;
inserting a front section and a mid section of a shaft portion of a bone screw through a through hole of a bone plate and through the cavity, and engaging the front section of the shaft portion with a far cortex of the bone such that a neck section of the shaft portion spans the cavity, wherein the front section has a core diameter and an outer thread diameter, the mid section has a core diameter and an outer non-threaded diameter, and the neck section has a diameter less than the outer non-threaded diameter of the mid section, the neck section defining a portion of the shaft having a length to span a thickness of a near cortex of the bone; and
engaging a head portion of the bone screw with the through hole of the bone plate; wherein the shaft portion is integral with the head portion.

29. The method of claim 28, wherein said establishing comprises initially establishing the cavity with a first diameter slightly smaller than the diameter of the front section, and then enlarging the cavity to a second diameter with a cutting feature present on the bone screw.

30. The method of claim 29, wherein the mid section comprises the cutting feature defining the outer non-threaded diameter.

31. The method of claim 29, wherein the cutting feature is present on the front section.

32. The method of claim 28, wherein said establishing is integrally performed when performing said inserting.

33. A bone screw, comprising:
  a shaft portion having
    a front section having a core diameter and including a plurality of threads threaded around the core diameter, the threads defining an outer thread diameter, for engagement of the bone screw with the far cortex of the bone,
    a mid section, and
    a neck section having a diameter less than the core diameter of the front section, the neck section defining a portion of the shaft having a length to span a thickness of a near cortex of the bone; and
  a head portion adjoining the shaft portion and providing for positive locking engagement of the bone screw with a bone plate; wherein the shaft portion is integral with the head portion.

34. The bone screw of claim 33, wherein the shaft portion is configured to provide an amount of elastic deflection to the mid section in a direction perpendicular to a axis of the shaft portion.

* * * * *